(12) United States Patent
Gibson et al.

(10) Patent No.: US 8,822,175 B2
(45) Date of Patent: Sep. 2, 2014

(54) WATER MONITORING SYSTEMS

(75) Inventors: Colin Gibson, Rhiwbina (GB); Gerald Melville Aubrey Jones, Swindon (GB); Francisco Gomez, Cheltenham (GB); John Thomas Magee, Quakers Yard (GB); David Tallis Pooley, Hayle (GB); William Ralph Craig Stewart, Llandaff (GB)

(73) Assignee: Cymtox Limited, Cardiff (GB)

( * ) Notice: Subject to any disclaimer, the term of this patent is extended or adjusted under 35 U.S.C. 154(b) by 1327 days.

(21) Appl. No.: 11/915,232

(22) PCT Filed: May 17, 2006

(86) PCT No.: PCT/GB2006/001803
§ 371 (c)(1),
(2), (4) Date: Oct. 3, 2008

(87) PCT Pub. No.: WO2006/125954
PCT Pub. Date: Nov. 30, 2006

(65) Prior Publication Data
US 2009/0215110 A1    Aug. 27, 2009

(51) Int. Cl.
*C12Q 1/02* (2006.01)
*C12Q 1/04* (2006.01)
*C12Q 1/06* (2006.01)
*C12M 1/34* (2006.01)
*C12M 3/02* (2006.01)
*C12M 1/00* (2006.01)
*G01N 21/77* (2006.01)
*G01N 33/18* (2006.01)
*C12M 1/36* (2006.01)
*C12M 1/32* (2006.01)

(52) U.S. Cl.
CPC ............ *G01N 21/77* (2013.01); *G01N 33/1866* (2013.01)
USPC ......... 435/34; 435/29; 435/287.9; 435/288.1; 435/288.3; 435/288.7

(58) Field of Classification Search
USPC ......... 435/29, 34, 287.9, 288.1, 288.3, 288.7, 435/808
See application file for complete search history.

(56) References Cited

U.S. PATENT DOCUMENTS

| | | | |
|---|---|---|---|
| 3,370,175 A | 2/1968 | Jordon et al. | |
| 5,362,642 A | 11/1994 | Kern | |
| 5,441,873 A | 8/1995 | Knight et al. | |
| 7,939,325 B2 | 5/2011 | Adams, Jr. et al. | |

FOREIGN PATENT DOCUMENTS

| | | |
|---|---|---|
| EP | 0757244 | 2/1997 |
| GB | 1 437 458 | 5/1976 |
| GB | 2 005 018 | 4/1979 |
| GB | 2005018 | 4/1979 |
| JP | 2000028602 A | 1/2000 |
| WO | WO9305142 | 3/1993 |
| WO | WO 03/008532 | 1/2003 |

OTHER PUBLICATIONS

Lee Baek-Seok et al.: "Statistical optimization of bioluminescence of *Photobacterium phosphoreum* KCTC2852" Journal of Bioscience and Bioengineering, vol. 92, No. 1, 2001, pp. 72-76.
Heitzer Armin et al: "Optical biosensor for environmental on-line monitoring of naphthalene and salicylate bioavailability with an immobilized bioluminescent catabolic reporter bacterium" Applied and Environmental Microbiology, vol. 60, No. 5, 1994, pp. 1487-1494.
Pooley David T et al: "Continuous culture of photobacterium." Biosensors & Bioelectronics, vol. 19, No. 11, Jun. 15, 2004, pp. 1457-1463.
Choi Kyungho et al: "Toxicity evaluation of metal plating wastewater employing the Microtox(R) assay: A comparison with cladocerans and fish" Environmental Toxicology, vol. 16, No. 2, Apr. 2001, pp. 136-141.
Faria Elsa Correia et al.: "Water toxicity monitoring using *Vibrio fischeri*: A method free of interferences from colour and turbidity." JEM Journal of Environmental Monitoring, vol. 6, No. 2, Feb. 2004, pp. 97-102.
Dyk Van T K et al: "Rapid and Sensitive Pollutant Detection by Induction of Heat Shock Gene-Bioluminescene Gene Fusions" Applied and Environmental, Microbiology, Washington, DC, US, vol. 60, No. 5, May 1994, pp. 1414-1420.
Perego P et al: "Applications of luminous bacteria on environmental monitoring" Chemical and Biochemical Engineering Quarterly Croation Soc. Chem. Eng Croatia, vol. 16, No. 2, 2002, pp. 87-92.
Kelly C J et al: "Bioluminescent Reporter Bacterium for Toxicity Monitoring in Biological Wastewater Treatment Systems" Water Environment Research, Water Environment Federation, Alexandria, VA, US, vol. 71, No. 1, Jan. 1999, pp. 31-35.
EP Application No. 06 727 128.8 Communication dated May 10, 2011.
Man Bock Gu, et al., "A Two-Stage Minibioreactor System for Continuous Toxicity Monitoring." Biosensors & Bioelectronics 14 (1999) 355-361 Feb. 8, 1999.
Final Office Action for U.S. Appl. No. 13/265,199 dated Feb. 14, 2014.

*Primary Examiner* — Jon P Weber
*Assistant Examiner* — Kailash C Srivastava
(74) *Attorney, Agent, or Firm* — King & Schickli, PLLC

(57) ABSTRACT

The invention relates to a continuous water monitoring system, including components thereof, and a method relating thereto for continuously monitoring, in real-time, a water supply in order to detect contaminants therein. The system employs the use of a live culture of bioluminescent bacteria and suitable light detecting means.

27 Claims, 3 Drawing Sheets

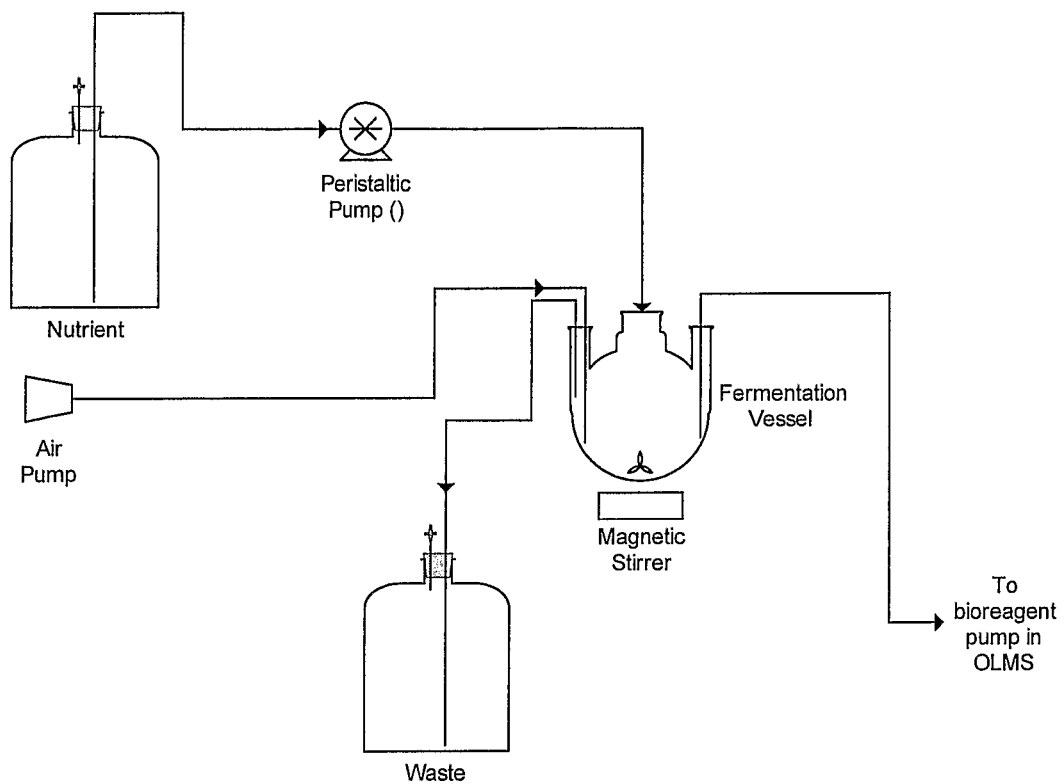
FIGURE: 1

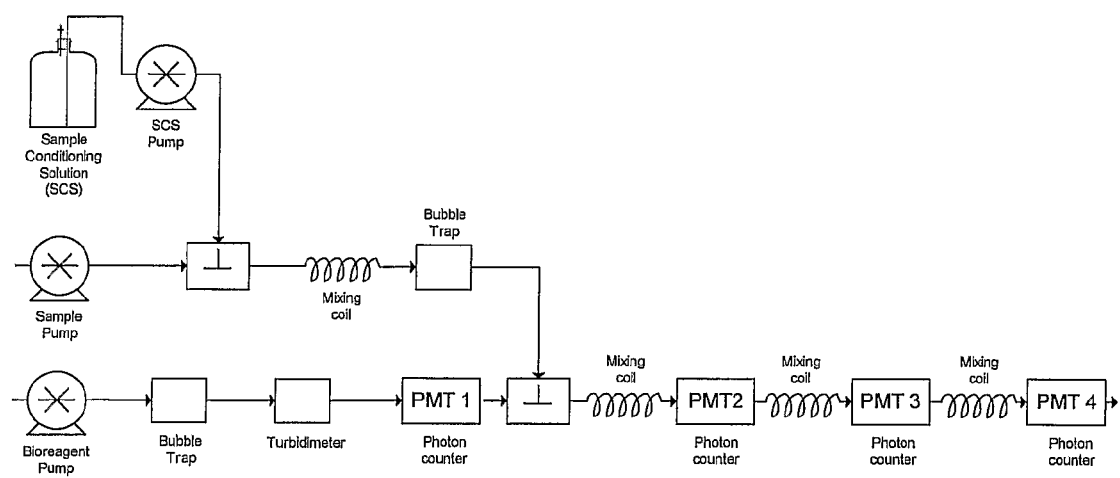
FIGURE: 2

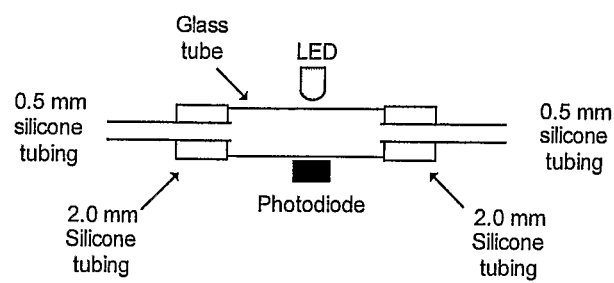
FIGURE: 3

WATER MONITORING SYSTEMS

The invention concerns a method for monitoring contaminants in water; and an apparatus for monitoring contaminants in water, including component parts thereof.

The invention has particular application in the monitoring of a water supply in an inhabited building or dwelling, however, it is also relevant to the monitoring of industrial water either before entering an industrial plant or thereafter. Moreover, the invention is also relevant to the monitoring of environmental water including naturally occurring rivers, streams, lakes, reservoirs and, even, sea water.

The concern for monitoring water quality has increased throughout the developed world, becoming a key security issue world-wide. For this reason, toxicity testing of water sources has become a very important subject, where gaining accurate, real time continuous results is of great interest. The present market leading technology, called MicroTOX, is a laboratory batch system which produces results in about 30 minutes and relies on the use of bacteria rejuvenated from a freeze-dried source.

Moreover, the US Environmental Protection Agency has recently produced a report which evaluates technologies and techniques that act as early warning systems for monitoring and evaluating drinking water quality. The report concludes that there is a need to provide a system suitable for this purpose and so endorses our belief that there is a need in the developed world to provide a real-time, continuous water monitoring system which can be deployed in a vast range of situations but, not least, in buildings or dwellings where the continuous monitoring of a water supply will serve as a deterrent to terrorist activity and also possibly save the lives of individuals should a water supply become contaminated for whatever reason.

There is also a need to provide a real-time, continuous, water monitoring system for use in the laboratory, at the least, for providing a first indication of water purity prior to, or instead of, undertaking further testing.

A continuous water monitoring system requires a continuously active detector. Moreover, the detector has to be sensitive to a range of contaminants but, in particular, contaminants that are dangerous to the health and existence of a living being. It is known to use aquatic vertebrates to monitor water supply but this presents problems, not least, in terms of maintaining the vertebrate population on a commercially viable scale.

We have therefore developed a system using light emitting bacteria. Most bioluminescent bacteria give off a blue-green light, while some give off a yellow light. None of these species are harmful. *Vibrio fischeri* is a bioluminescent marine bacterium that commonly inhabits fish.

This bacterium has a Gram-negative cell wall, is motile by means of flagella, and the cell shape is a curved rod. Bacteria of the *Vibrio* genus have been found in association with squid, nematodes, microscopic organisms, and with insects that feed on nematodes. Some gather in the pockets of fish in a symbiotic relationship. The fish are luminous because of the photobacteria.

The occurrence of luminescence is due to the bacterial cells' electron transport system, involving an aldehyde, an enzyme, oxygen, and an altered form of riboflavin. Though Vibrio isolates are facultative anaerobes, they are bioluminescent only when $O_2$ is present. Several components are needed for bacterial bioluminescence: the enzyme luciferase, a long-chain aliphatic aldehyde, flavin mononucleotide (FMN), and $O_2$. The primary electron donor is NADH, and the electrons pass through FMN to the luciferase. The reaction can be expressed as:

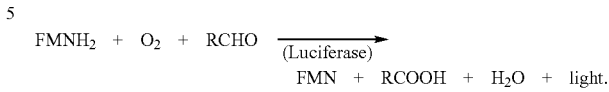

$$FMNH_2 + O_2 + RCHO \xrightarrow{\text{(Luciferase)}} FMN + RCOOH + H_2O + \text{light}.$$

The light-generating system constitutes a bypass route for shunting electrons from FMNH2 to $O_2$, without involving other electron carriers such as quinones and cytochromes.

The enzyme luciferase shows a unique kind of regulatory synthesis called autoinduction. The bioluminous bacteria produce a specific substance, the autoinducer, which accumulates in the culture medium during growth, and when the amount of this substance has reached a critical level, induction of the enzyme occurs. The autoinducer in *V. fischeri* has been identified as N-β-ketocaproylhomoserine lactone. Thus cultures of bioluminous bacteria at low cell density are not bioluminescent, but become bioluminescent when growth reaches a sufficiently high density so that the autoinducer can accumulate and function. Because of the autoinduction phenomenon, it is obvious that the free-living bioluminescent bacteria in seawater will not be bioluminescent because the autoinducer could not accumulate; bioluminescence only develops when conditions are favourable for the development of high population densities. Although it is not clear why bioluminescence is density dependent in free-living bacteria, in symbiotic strains of bioluminescent bacteria, the rationale for density-dependent bioluminescence is clear: bioluminescence only develops when sufficiently high population densities are reached in the light organ of the fish to allow a visible flash of light.

Much new information about bioluminescence has emerged from studies of the genetics of this process. Several lux operons have been identified in bioluminescent *Vibrio* species, and the key structural genes cloned and sequenced. The luxA and the luxB genes code for the a and b subunits, respectively, of bacterial luciferase. The luxC, luxD, and the luxE genes code for polypeptides that function in the bioluminescence reaction and in the generation and activation of fatty acids for the bioluminescence system.

We have therefore exploited and optimised the characteristics of bioluminescent bacteria in order to provide a detection system which is sensitive to a wide range of toxic contaminants. The test criteria for the detection of these contaminants is typically a decrease in luminescence measured after at least one selected time interval. Moreover, we have favoured a species of bacteria which is commonly used for toxicity batch analysis in laboratories, i.e. *Vibrio fischeri*.

As implied above, our challenge has been to maintain a continuous, regenerative, population of this bacteria in order to provide a continuous monitoring system. Our invention has therefore involved the production of i) a fermenter that will keep the population of bacteria alive and in a regenerative mode and also ii) an on-line monitoring system. By the term on-line, we mean a system that is continuously sampling a supply of water to be monitored. In a building, this will typically involve diverting a sample of a mains water supply to our on-line monitoring system.

Whilst a number of workers in the field have attempted to produce a continuous, on-line monitoring system to detect contaminants in a water supply, we are the first to achieve this objective.

Our work has been difficult because we have had to balance a number of variables in order to arrive at a system that works. Moreover, we have had to experiment with the detailed configuration of the system in order to produce a specification that will support a bacterial population and continuously feed a fresh supply of bacteria, with the required quality specifications, to our on-line monitoring system.

As a result of our endeavours we have been able to produce a continuous, on-line water monitoring system for measuring, in real-time, the presence of contaminants in a water supply.

STATEMENTS OF INVENTION

According to a first aspect of the invention there is therefore provided a continuous water monitoring system for detecting contaminants in a water supply comprising:
a) a feed line for delivering a sample of water from a water system or a natural water supply to a test chamber;
b) a test chamber;
c) a bioreagent fermenter in fluid communication with said test chamber for delivering a light emitting bioreagent, grown in said fermenter, to said test chamber;
d) a light detection means associated with at least said test chamber for measuring light emitted from said bioreagent;
e) a waste line for removing said sample and said bioreagent from said test chamber; characterised in that:
said light detection means measures the light emitting properties of the bioreagent before and after contact with said water sample and, where there is a change in said light emitting properties after contact with said sample, the water monitoring system registers that the sample water has been contaminated.

According to a second aspect of the invention there is provided a continuous water monitoring system for detecting contaminants in a water supply comprising:
a) a feed line for delivering a sample of water from a water system or a natural water supply to a test chamber;
b) a test chamber;
c) a bioreagent fermenter in fluid communication with said test chamber for delivering a light emitting bioreagent, grown in said fermenter, to said test chamber;
d) a light detection means associated with at least said test chamber for measuring light emitted from said bioreagent; and
e) a waste line for removing said sample and said bioreagent from said test chamber; characterised in that:
f) a water sample conditioning means is provided for conditioning said sample of water before it is delivered to said test chamber.

In a preferred embodiment of either aspect of the invention the light detection means may be associated solely with said test chamber and so a sample of bioreagent is held in said test chamber and a determination of light emission is determined prior to the sample being mixed therewith. Additionally, or alternatively, the light detection means, or a further light detection means, may be associated with said bioreagent fermenter, or a line leading therefrom, so that the light emitting properties of said bioreagent can be determined prior to the bioreagent entering the test chamber in addition to a determination of the light emitting properties of the bioreagent being determined after the sample has been added thereto. Accordingly, said light detection means may comprise a single means associated with either, or both, said test chamber and/or a means for delivering said bioreagent from said bioreagent fermenter to said test chamber; or, alternatively, a plurality of light detection means may be provided, at least one of which is associated with said test chamber and at least another of which is associated with the means for transferring a bioreagent from said fermenter to said test chamber.

In the second aspect of the invention said water sample conditioning means alters the property of the water sample so as to make it biocompatible with the bioreagent. Most preferably, the water sample conditioning means alters the ionic strength of the water sample so that it will be bio-compatible with the bioreagent and so, typically, changes the salinity of the water sample. Additionally, and advantageously, the water sample conditioning means also alters the ionic concentration of at least one selected ion and, most preferably, removes anti bacterial compounds generated by chlorination, chloramination or ozone treatment of the water supply at source.

In a preferred embodiment of either aspect of the invention the bioreagent is a population of light emitting bacteria and, in particular, bioluminescent bacteria. This bacteria may be naturally occurring or genetically modified or produced so as to have the requisite qualities for operating in the system of the invention and, in particular, the requisite light emitting properties and/or sensitivity to contaminants. More preferably still, bioreagents suitable for use in the water monitoring system of the invention include any one or more of the following bacteria: *Photobacterium* species; *Vibrio* species; and *Xenorhabdus* species. Indeed, any species that is engineered to be luminescent is contemplated.

Most typically, the bacteria are selected so as to be sensitive to the contaminants by way of exhibiting a reduction in their light emitting properties. This, most typically, will be due to the decline or death of the bacterial population. However, in an alternative embodiment of the invention, it is possible to use bacteria that produce enhanced light emission in response to the presence of a particular contaminant. In this instance, the bacterial population could be detecting bionutrients.

It will be apparent to those skilled in the art that the above arrangements provide for a test chamber in which a sample of water and a sample of bioreagent can be combined in order to test for contaminants. After the test has been performed the mixed solution is removed from the test chamber via the waste line and is, ultimately, removed from the system. Simultaneously, or shortly thereafter, or even at a predetermined internal thereafter, a further sample of bioreagent and a further sample of water is fed to the test chamber so that the detection of contaminants can be repeated. In this way, a sample of water can be continuously monitored.

In a preferred embodiment of either aspect of the invention a segmenting means is provided whereby a water supply is sampled in a segmented fashion, by this we mean that segments of water are isolated for the purpose of sampling. Most typically, we undertake this segmentation by inserting, at pre-determined intervals, bubbles of air.

In a preferred embodiment of either aspect of the invention a pump means is provided for driving either, or both, of said sample of water and sample of bioreagent through the system.

In yet a further preferred embodiment of either aspect of the invention said fermenter is a continuous culture system. Our continuous culture system has constant volume: a continuous inflow of fresh medium and the spent culture medium is removed continuously, ideally, at a constant rate. Once a continuous culture system reaches steady state (equilibrium), the cell number and nutrient status remain constant. There are different kinds of continuous culture systems, for our particular case, it was decided to operate the fermenter as a chemostat which controls both the population density and the growth rate of the culture.

Growth is defined as the increase of the number of microbial cells (biomass) in a population. The bacterial cell is a synthetic machine that is able to duplicate itself. An individual cell grows continuously until the cell divides into two new cells (binary fission). During this cycle all the structural components of the cell double. The time required for a complete growth cycle in bacteria is highly variable and is dependent on a number of factors, both nutritional and genetic. The growth rate is the parameter that measures the change in cell number or cell mass per unit time. It should be noted that the generation time of any given organism is dependent to some extent on the growth medium used and the incubation conditions employed.

Most advantageously; the fermenter includes an anti growback device in order to prevent the grow-back of biofilms towards the source of fermenter nutrient supply. The anti grow-back device, typically, comprises a barrier that stops the bacteria from passing from the fermenter into the nutrient feed line and may simply comprise a gap wherein the end of the feed line is spaced remotely from the bacterial culture. The fermenter also comprises an air inflow and an air outflow line in order to keep a fresh supply of air in contact with the bacterial population. A culture overflow line is also provided to keep a constant volume of culture inside the fermenter.

Advantageously, lines leading to and from the fermenter are made from a material, or include an additive, such as silver, which inhibits microbial growth and so has biocidal properties. This characteristic of the feed lines or overflow lines means that biofilm growth in the lines is eliminated, or certainly reduced.

In our preferred embodiments of the invention we operate our fermenter as a chemostat. However, it may be operated as, for e.g. a luminostat or turbidostat.

There are two key factors in the control of a chemostat: the dilution rate and the concentration of a limiting nutrient. One of the major advantages of a chemostat type fermenter is that the growth rate and the cell density can be controlled independently of each other. The growth rate is controlled by adjusting the dilution rate and the cell density by varying the concentration of a nutrient present in a limiting amount.

There are wide limits over which the dilution rate controls growth rate, i.e. any desired growth rate can be obtained in the chemostat by simply varying the dilution rate. But at very low and very high dilution rates, the equilibrium of the system breaks down. At high dilution rates, the organisms cannot grow fast enough to keep up with its dilution, and the culture is washed out of the fermenter. On the other hand, at very low dilution rates, a large fraction of the cells may die from starvation because the limiting nutrient is not being added fast enough to permit maintenance of cell metabolism. Similarly, the population density may be set by varying the concentration of a single nutrient in the medium reservoir.

The cell density (cells/ml) in the fermenter can be controlled by the level of the limiting nutrient. If the concentration of this nutrient in the incoming medium is raised, with the dilution rate remaining constant, the cell density will increase.

The amount of bacteria that can be produced in a fermenter depends on the growth rate of the specie and the volume of culture.

Other workers have reported that *V. fischeri* grow best at 23° C. in the presence of 3% salt.

As mentioned, in either aspect of the invention our water monitoring system includes an on-line monitoring component which monitors the luminescence of the bioreagent after it is mixed with a sample. Ideally, the on-line monitoring system is adapted to detect light emission using a plurality of photon counting devices which, ideally, are operated in a time delay fashion so that each photon counting device, or group thereof, makes a determination of light emission at a predetermined time after the point when the sample and the bioreagent are mixed. Additionally, it is preferred for a further photon counting device to be used to measure the light emitting properties of the bacteria prior to mixing same with the water sample. A comparison of this first pre-mixing reading with any further readings provides an indication of a reduction or enhancement, if any, of the bioluminescence. Typically, a reduction is observed where contaminants are present and the reduction is referred to as an inhibition ratio.

In yet a further preferred embodiment of the invention the aforementioned pump means comprises a multi-channel peristaltic pump which is operated at a relatively high pulse rate in order to provide for a relatively smooth flow of the samples through the system.

In yet a further preferred embodiment of the first aspect of our invention, our water monitoring system additionally comprises a water sample conditioner. The conditioner modifies the sample of water to be tested in order to ensure that it is biocompatible with the bioreagent to be used in the water monitoring system. Thus, the water sample conditioner alters the ionic concentration of the water sample, typically increasing the salinity of same and also, preferably, removing any particles that interfere with or alter the sensitivity of the bioreagent to the sample. For example, the water sample conditioner will remove chloride ions or the products of chlorination or chloramination which have a negative effect upon the light emitting properties of most bacteria.

In yet a further preferred embodiment of either aspect of the invention the water monitoring system includes at least one bubble trap, ideally, selectively positioned, to remove pockets of air that would otherwise interfere with the light detection mechanism.

In yet a further preferred embodiment of either aspect of the invention said fermenter and/or said test chamber includes an agitator or stirrer for ensuring that air, or oxygen, is equally distributed in the medium supporting the bioreagent.

Yet more preferably still, the water monitoring system of either aspect of the invention includes a turbidimeter which monitors the turbidity of the bacterial culture in order to determine the cell density inside the fermenter. The turbidimeter may be provided in association with the fermenter or downstream therefrom.

In yet a further preferred embodiment of either aspect of the invention there is provided a pre-filtration unit in order to filter a water sample that is to be tested.

In yet a further preferred embodiment of either aspect of the invention there is provided a pre- and/or post-sample concentration means for concentrating a sample to be tested. Thus, the pre-sample concentration means concentrates a sample of water prior to it being tested and this concentrates any contaminants that may be in the water. A post-sample concentration means concentrates a sample after it has been tested so that it can be further tested or analysed and, indeed, it may be fed back to the test chamber of the invention with a view to a further measurement being taken. As a man skilled in the art will appreciate, this post-sampling concentration means may be selectively activated, most typically, by the selective flow of a sample through the post-sampling concentration means using suitable valve means.

According to a third aspect of the invention there is provided a method for continuously monitoring a water supply in order to detect contaminants therein comprising:
a) delivering a sample of water from a water system or a natural water supply to a test chamber;
b) delivering a light emitting bioreagent to said test chamber;

c) detecting light emitted from said bioreagent before and after it has been exposed to said water sample;
d) determining, where there has been a change in light emission as a result of contact of said bioreagent with said water sample, that contaminants exist in said water sample; and
e) removing said water sample and said bioreagent from said test chamber in order to repeat the above process.

According to a further aspect of the invention there is provided a continuous water monitoring system for detecting contaminants in a water supply comprising:
a) a feed line for delivering a sample of water from a water system or a natural water supply to a test chamber;
b) a test chamber;
c) a water sample conditioning means for altering the ionic strength of said sample of water before it is delivered to said test chamber;
d) a bioreagent fermenter in fluid communication with said test chamber for delivering a light emitting bioreagent, Vibrio fischeri, grown in said fermenter to said test chamber;
e) a light detection means associated with at least said test chamber for measuring light emitted from said bioreagent; and
f) a waste line for removing said sample and said bioreagent from said test chamber.

According to a further aspect of the invention there is provided a continuous water monitoring system, or components thereof, as substantially herein described and with reference to the following Figures.

According to a yet further aspect of the invention there is provided a method for continuously monitoring a water supply as substantially herein described and with reference to the following Figures.

An embodiment of the invention will now be described, by way of example only, with reference to the following figures wherein:

FIG. 1 is a diagrammatic representation of a first component of the water monitoring system of the invention and, essentially, shows the bioreagent fermenter;

FIG. 2 is a diagrammatic representation of a second component of the water monitoring system and, essentially, shows the on-line monitoring subsystem; and FIG. 3 shows a turbidimeter assembly diagram.

A diagram illustrating the bacterial production system used for growing the bioreagent is presented in FIG. 1. A 250 ml glass spherical bottle with three necks was used for the fermenter vessel. The central bottle neck was used to connect the feeding line which supplies the nutrient broth for the culture. Because the used species is likely to form biofilms and tends to growth back towards the source of the nutrient, an anti growth back device was implemented to isolate the fermenter from the medium bottle. The anti growth back device was built by using a No. 16 needle which drips the nutrient into the centre of the culture, creating an air barrier that stop the bacteria from passing from the fermenter into the feeding line.

The air inflow and the culture overflow lines were connected to one of the side necks of the fermenter vessel by using a perforated rubber stopper. In order to pass through the stopper, stainless steel tubes were used. All of the lines connected to the fermenter were made of, or included, biocidal materials in order to prevent biofilm growth therein. The air inflow was connected using 2 mm OD tubing, while the overflow was connected using 5 mm OD tubing. Since oxygen at concentrations above 0.5 mg/L is required for bioluminescence, a continuous air inflow is supplied through a sparge tube which is immersed in the centre of the culture. In order to promote the oxygen diffusion in the medium, the culture is continuously stirred. It should be noted that bacterial luminescence is highly sensitive to variations in oxygen concentrations below 0.5 mg/L. The supplying of the minimum required oxygen is a key issue to warranting a good quality bioreagent.

The overflow line is used to keep a constant volume of culture inside the fermenter and as air outflow. The level is controlled by locating the outflow at the desired height. When the level inside the vessel increases, due to an increase in the nutrient inflow or to a reduction in the demand for bioreagent, and the culture reaches the outflow, the excess volume is flushed out by the positive pressure created by the air inflow.

The bioreagent supply line was connected on the other side bottle neck. This line supplies freshly cultured bacteria to the on-line monitoring system.

In FIG. 2 there is shown a diagrammatic illustration of the light detecting on-line monitoring subsystem.

The On-Line Monitoring System (OLMS) is the system responsible for monitoring the luminescence of the bioreagent before and after it is mixed with a sample. The light emission after mixing is ideally, but not exclusively, determined by means of 3 photon counting devices located or operated at 3 seconds, 15 seconds and 30 seconds after the point were the sample and the bioreagent are mixed. In some embodiments a single photon counting device may be employed. Moreover, light emission may be measured at any one or more of a selected time interval(s), ideally, within a 30-second interval. The changes in the light emission are monitored by the means of a calculated variable that takes in consideration the initial emission of the bioreagent before being mixed with the sample. This variable is referred as the inhibition ratio. In an alternative embodiment of the invention, the photon counters PMT1, PMT2, PMT3, and PMT4 may be replaced with fibre optic sensors. These sensors feed their signals to one master photon counter. The signals are sequenced and tagged to allow subsequent signal analysis and interpretation. This latter arrangement is most favourably used with what we term a segmented system where we, effectively, isolate samples as segments from a continuous sample feed by, typically, the deliberate metered insertion of air bubbles. This segmenting of the system enables us to take pulsed readings and interpret signals with either discreet photon counters or with optic fibre centres feeding one counter. Moreover, the use of the system in this segmented fashion enables for the use of flushing segments during monitoring and, even, the use of control segments with which to compare the results of test segments. Segmentation further, advantageously, allows not only flushing using anti bacterial agents but also accurate determination of the nature of the contaminant by the use of a contaminant anti-toxin such as a heavy metal chelator in order to chelate heavy metals that may be poisoning the system and so killing the bacterial population.

Those skilled in the art will appreciate that the use of multiple photo detectors enables an analysis of the nature of the contaminant affecting the bioluminescent emission, for example, the nature and the concentration of the toxin may be deduced from the characteristics of the inhibition spectra such that a contaminant such as cyanide will act quickly giving an abrupt rise in inhibition up to a plateau where the bacterial population is killed. In contrast, heavy metals will act much more slowly, even at high concentrations, thus giving a much longer and shallower curve prior to an inhibition plateau being reached.

Using the system of the invention we can also take advantage of stopping the flow through the system once a toxic contaminant is detected. In this way, after the flow is stopped, the time course of an inhibition can be measured using any of the post-mixing photo detectors over a long period (in the order of minutes) to affirm a real toxic effect and also to determine the time course of the level of inhibition: both crucial indicators of the nature of the toxin.

As mentioned, the system may also be used for the addition of toxin-specific anti-toxin reagents.

The sample and the bioreagent are pumped by a multi-channel peristaltic pump with an eight rollers head. Using a multi-channel pump has the advantage of reducing the cost of the system by pumping multiple streams with the same pump. But on the other hand, it imposes the constraint that the mixing ratios of bioreagent and sample can only be adjusted by changing the bore of the manifold tubes. Thus, the mixing ratios are limited to the manifold tubing sizes supplied by the manufacturer. As an alternative, a number of pumps may be used. This latter embodiment enables the mixing ratios to be changed.

The analyser is configured to monitor fresh water, but as a consequence of the bioreagent being based in a marine environment, the salinity of the sample has to be equalized to that of the culture media if optimum sensitivity and performance is to be achieved. If the ionic conditions of the media where the bacteria is living are drastically changed (reduced or increased), an osmotic shock will occur killing most of the population. In order to avoid reductions in the osmotic pressure of the mixture (after mixing the sample and the bioreagent) the sample has to be preconditioned by mixing it with a concentrated sodium chloride solution. The preparation of a sample conditioning solution is elaborated hereinafter.

As was mentioned previously, the basic measurement of the acute toxicity monitor is the inhibition ratio. This is a calculation of how much the light emission of the bioreagent has changed, in percentage points, after being mixed with the sample. The light emission of the bioreagent, just before the mixing point, is therefore used as the reference. The equation used for the calculation of the inhibition ratio is:

$$\text{Inhibition ratio } (\%) = 1 - \frac{PMT_x}{PMT_1} \times 100. \quad (1)$$

Where $PMT_1$ is the photon counting measurement reported by the photon counting devices located before the mixing point and $PMT_x$ is the photon count for each one of the three photon counters located at 3, 15 and 30 seconds after the mixing point.

The peristaltic pump used for the OLMS is a Multi-channel peristaltic pump (pump model: 505U, head model: 308MC) manufactured by Watson-Marlow. Peristaltic pumps have good flow rate accuracy and are the best option when sterile solutions have to be dealt with. The whole system can be assembled, autoclaved and later installed in the pumps without breaking the sterility of the system. On the other hand, peristaltic pumps have the disadvantage that the flow pattern is not continuous but pulsed. The pulsating flow effect is enhanced at low pump speeds. Because, the OLMS is using photon counting devices for measuring light emission, the numbers of photon will change if the flow rate changes. In order to minimise fluctuations in the photon counts due to pulsating flow, it is advisable to run the pump at maximum speed (55 RPM).

The OLMS has to deal with three streams: the sample, the bioreagent and the sample conditioning solution. The bioreagent-sample dilution ratio was determined by trying different tube sizes available by the manufacturer until a suitable ratio was found. The bioreagent is being pumped by using 0.25 mm ID manifold tubing (color code: blue-orange). The sample is being pumped by a 0.88 ID (colour code: Orange-Orange).

These tubes have nominal flow rates of 0.23 ml/min for the bioreagent and 2.6 ml/min for the sample. The concentration of bioreagent after mixing it with the sample is between 50%-5% and ideally 7.52%.

Frequent air bubbles were observed in the sample line and in the bioreagent line. Air bubbles cause negative peaks in the photon count because the bubbles are empty sections where no photons are emitted. Depending on the size of the air bubbles, the blank spaces can generate false positives in the monitoring system.

The presence of air bubbles was addressed by introducing air liquid separators in the reagent and sample lines after the discharge of the pump (see FIG. 2). The effectiveness of the air-liquid separator in removing the air bubbles is 100%. An additional advantage of using an air-liquid separator is that the air gap, inside the separator chamber, acts as a pulse damper, reducing the pulsating effect caused by the rollers of the pump. On the other hand, the introduction of an air liquid separator adds the disadvantage of having a dead volume inside the separator vessel and the need for a control system for controlling the liquid level by releasing the excess air through a vent. The liquid volume inside the vessel will determine the residence time. This is the time that it takes a particle to pass through the separation system. As a consequence, the residence time degrades the system by reducing the oxygenation of the bioreagent and by increasing the detection time. In order to reduce this side effect, the residence time has to be kept to a minimum.

The monitoring of a micro-organism's growth is a key parameter of any continuous culture system. The best method for obtaining an estimate of cell number is by use of turbidity measurements. The bacterial culture looks more turbid because the cells inside the culture scatter light passing through the solution. The higher the cell number, the greater the scatter; and hence the more turbid the solution. The turbidity can be measured by passing light through a cell suspension and measuring the amount of unscattered light that emerges. In order to monitor the cell density inside the fermenter, a turbidimeter was built and installed in the bioreagent line after the bubble trap (see FIG. 2). The light source was built by using a high intensity (2000 mcd) green LED. The intensity of the light source can be adjusted by means of a 10 kilo-ohm potentiometer connected in a voltage divided configuration. The LED was connected to a digital output for power supply and control purposes. For measuring the unscattered light a photodiode with an internal amplifier was used (OPT301). The gain of the amplifier was set to: $20 \times 10^6$ by using two 10 mega-ohm resistors. The photodiode requires a dual power source (+/−12 Vdc) and it returns an output in the range (0-10 Vdc). Two signals from the turbidimeter were monitored: the voltage applied to the LED and the voltage received by the photodiode.

The bacteria used as bioreagent is prone to grow on the inner wall of silicone tubes, forming biofilms. After 48 hours of continuous operation, biofilms have been seen in the tubes of the OLMS. These biofilms degrade the quality of the measurements reported by the photon counters, by blocking the light propagation. In addition, the inner diameter of the tubes is reduced. The reduction in the inner area of the tubing causes problems with flow rate and pressure across the system. As the time goes, the bacteria keep growing, the biofilm becomes thicker and the fluid velocity increases. The increase in fluid velocity increases drag forces, releasing biofilm clumps that plug downstream sections where the inner sections have been reduced due to the biofilm presence. To avoid the growth of biofilms to thickness that can damage the integrity of the OLMS, the system should be regularly flushed with an acidic solution, ideally, at intervals between 24 and 48 hours.

The bioreagent of the toxicity monitor is based on marine bacteria. These bio-organisms require a 3% salt concentration in order to perform their physiological functions. Because, the toxicity monitor, typically, is intended to sample fresh water, the salinity of the sample has to be increased in order to be biocompatible. Thus the water sample is mixed with a sodium chloride concentrated solution in order to equalize the sample osmotic conditions with the conditions of the culture. The proper concentration of the sample conditioning solution (SCS) will be determined by the sodium chloride concentration of the bioreagent (25 g/L). For instance, in our case the sample is being pumped at a nominal flow of 2.6 ml/min and the bioreagent at 0.23 ml/min. In order to calculate the concentration of the SCS, the following equation is used:

$$C_1 = \frac{V_2 C_2}{V_1} C1 = V2C2/V1, \quad (1)$$

where $V_1$ is the flow rate of the SCS, $C_1$ is the concentration of the SCS in g/L, $V_2$ is the flow rate of the sample+the SCS and $C_2$ is the NaCl concentration of the bioreagent. For the nominal flow case, the concentration of the SCS is: 307.61 g/L.

Drinking water is treated by adding antibacterial agents. There are three antibacterial processes that can be used for drinking water treatment: chlorination, chloramination and ozonation. From the listed options, the most used is chlorination. Chlorine is used for killing bacteria coming from water sources and a residual level is kept at 0.5-1.0 mg/L to protect the water from bacterial contamination during the transport process.

Due to its antibacterial properties, chlorine will interfere with the biosensor by killing the micro-organisms. If chlorine levels were constant, chlorine interference would not be a problem, but because chlorine levels in mains water vary constantly, these variations could be seen by the monitor as a toxicant and could generate false positives. In order to avoid this undesirable behaviour, chlorine can be removed from the sample by adding sodium thiosulfate ($Na_2S_2O_3$).

The amount of sodium thiosulfate needed for removing the chlorine from a water sample depends on the amount of free chlorine. Stoichiometric calculations can be carried out, but they are quite complicated to do and in order to have reliable results, all exogenous factors have to be considered. The dose used for conditioning the sample was taken from the Microtox user manual and the recommended concentration for treating the sample is 100 mg/L. For determining the amount of sodium thiosulfate that has to be added to the SCS, equation 1 has to be used. For the same flows used for the sodium chloride example, the concentration of sodium thiosulfate required in the SCS is: 1.23 g/L.

Although not shown, a man skilled in the art will appreciate that a filter may be used in the system to filter a sample of water to be tested in order to remove suspended solids and, most typically, substances that will affect the bioluminescence. Additionally a pre- and/or post-sampling concentration means may be provided where the water to be sampled is concentrated in order to increase the chances (pre-sampling) of detecting any contaminants. Moreover, a post-sampling concentration means may also, or alternatively, be provided so that if a reading is unsatisfactory the water sample can be concentrated before either an attempt is made to take another reading, using the existing bioreagent, or, new bioreagent is added and a reading taken.

We have tested our water monitoring system against a market standard which represents the Environment Protection Agency's benchmark for three reference substances: cyanide, thallium sulphate and chlorine and in each case we have shown that our system matches or betters the EPA benchmark conformance to 100%. See Table 1.

Additionally, to demonstrate the feasibility of "a 30 second detection time" via the indication of a "toxicity alarm" less than 30 seconds after the introduction to the PoC device of a test sample containing either 0.25 mg/L, cyanide or 240 ml/L thallium sulphate having previously introduced a test sample containing normally chlorinated water (chlorine concentrations between 0.2 and 1 mg/L, over many minutes/hours). The results presented in Table 2 show that our system matches or betters the EPA benchmark conformance to 100%.

To demonstrate the feasibility of "an eight week consumables cycle" via the automatic inoculation and establishment of a continuous luminescing culture within a first flow-through sub-system, the sensing of the pending end to adequate luminescence within that first flow-through sub-system and the subsequent automatic inoculation and establishment of a continuous luminescing culture within a second flow-through sub-system in such a way as to enable continuous toxicity measurements. The results are shown in Table 3. Conformance to the EPA benchmark was 100%.

We therefore consider that our water monitoring system provides a novel and inventive system for the continuous sampling of water in real-time.

TABLE 1

| Substance | Target | Conformance |
| --- | --- | --- |
| Cyanide | 0.25 mg/L (LD/1000) | 100% |
| Thallium Sulphate | 240 mg/L (LD/10) | 100% |
| Chlorine | no interference | 100% |

TABLE 2

| Substance | Target | Conformance |
| --- | --- | --- |
| Cyanide | 0.25 mg/L within 30 seconds | 100% |
| Thallium Sulphate | 240 mg/L within 30 seconds | 100% |

TABLE 3

| | Target | Conformance |
| --- | --- | --- |
| Consumables cycle | 8 week | 100% |
| Backup subsystem | Automatic start-up | 100% |

The invention claimed is:

1. A continuous water monitoring system for detecting contaminants in a water supply comprising:
   a) a feed line for delivering a sample of water from a water system or a natural water supply to a test chamber;
   b) a test chamber;
   c) a bioreagent fermenter in fluid communication with said test chamber for delivering a light emitting bioreagent sample, grown in said fermenter, to said test chamber;
   d) a light detection means for measuring light emitted from said bioreagent sample, comprising:
      at least one light detector upstream of said test chamber;

at least one other light detector downstream of said bioreagent fermenter and said test chamber; and optionally at least one third light detector connected through a fluid communication means downstream of said second light detector; and e) a waste line for removing said sample and said bioreagent sample from said test chamber;

wherein said light detection means measures the light emitting properties of the delivered bioreagent sample before and after contact with said water sample, and further wherein a change in said light emitting properties after contact with said water sample indicates that the water sample has been contaminated.

2. A continuous water monitoring system for detecting contaminants in a water supply comprising:

a) a feed line for delivering a sample of water from a water system or a natural water supply to a test chamber;

b) a test chamber;

c) a bioreagent fermenter in fluid communication with said test chamber for delivering a light emitting bioreagent sample, grown in said fermenter, to said test chamber;

d) a light detection means connected to at least said test chamber for measuring light emitted from said delivered bioreagent sample before contacting said bioreagent sample with sample water and subsequently after contact with said sample of water, said light detection means further comprising a plurality of sequentially arrayed photon counting devices in fluid communication with said test chamber which are operated in a time-delay fashion so that each one, or selected groups, of the photon counting devices makes a determination of light emission at one or more pre-determined times after said sample and said bioreagent are mixed in said test chamber; and e) a waste line for removing said sample of water and said bioreagent sample from said test chamber;

wherein a change in the light emitting properties of the bioreagent sample indicates that the water sample is contaminated.

3. A continuous water monitoring system according to claim 1 or 2, wherein there is provided a water sample conditioning means that alters the property of the water sample so as to make it bio-compatible with the bioreagent.

4. A continuous water monitoring system according to claim 1 or 2, wherein the water sample conditioning means alters the ionic strength of the water sample.

5. A continuous water monitoring system according to claim 1 or 2, wherein the water sample conditioning means alters the ionic concentration of at least one selected ion.

6. A continuous water monitoring system according to claim 1 or 2, wherein said water sample conditioning means removes anti-bacterial compounds generated by chlorination or chloramination or ozone treatment of the water supply.

7. A continuous water monitoring system according to claim 1 or 2, wherein said bioreagent is a light emitting bacterium.

8. A continuous water monitoring system according to claim 7, wherein said bacteria is a bio-luminescent bacterium.

9. A continuous water monitoring system according to claim 7, wherein said bacteria is of the Genus *Photobacterium*, *Vibrio*, or *Zenorhabdus*.

10. A continuous water monitoring system according to claim 1 or 2, wherein a gaseous means is associated with said feed-line whereby bubbles of gas can be inserted into said water sample at pre-selected intervals in order to segment said water sample into discrete amounts of water for sampling.

11. A continuous water monitoring system according to claim 1 or 2, wherein pump means is provided for driving either, or both, of said sample of water or said bioreagent through said system.

12. A continuous water monitoring system according to claim 1 or 2, wherein said fermenter is operated as a continuous culture system.

13. A continuous water monitoring system according to claim 12, wherein said fermenter is operated as a chemostat.

14. A continuous water monitoring system according to claim 1 or 2, wherein said fermenter includes an anti growback device to prevent the grow-back of biofilms towards the source of a nutrient supply.

15. A continuous water monitoring system according to claim 1 or 2, wherein said fermenter comprises an air inflow and an air outflow line.

16. A continuous water monitoring system according to claim 1 or 2, wherein said fermenter comprises a culture overflow line whereby the volume within the fermenter is kept constant.

17. A continuous water monitoring system according to claim 1 or 2, wherein said line, or lines, or means for delivering bioreagents are made from a material which inhibits bacterial growth.

18. A continuous water monitoring system according to claim 1, wherein said light detection means further comprises a plurality of sequentially arrayed photon counting devices which are operated in a time-delay fashion so that each one, or selected groups, of photon counting devices makes a determination of light emission at a pre-determined time after the point when said sample and said bioreagent are mixed.

19. A continuous water monitoring system according to claim 18, wherein said light detection means further comprises at least one photon counting device for measuring light emitted from said bioreagent prior to the mixing of same with said water sample.

20. A continuous water monitoring system according to claim 1 or 2, wherein said system comprises at least one bubble trap to remove pockets of air that would otherwise interfere with the light detection mechanism.

21. A continuous water monitoring system according to claim 1 or 2, wherein said fermenter and/or said test chamber includes an agitator.

22. A continuous water monitoring system according to claim 1 or 2 which further includes a turbidimeter which monitors the turbidity of the bioreagent in order to determine cell density inside said fermenter.

23. A continuous water monitoring system according to claim 1 or 2, wherein there is provided a pre-filtration means for filtering said water sample prior to the testing thereof.

24. A continuous water monitoring system according to claim 1 or 2, wherein there is further provided a pre-sample concentration means which concentrates said sample prior to the testing thereof.

25. A continuous water monitoring system according to claim 1 or 2 which further comprises a post-sample concentration means which concentrates said sample after the testing thereof.

26. A method for continuously monitoring a water supply in order to detect contaminants therein comprising:

a) delivering a sample of water from a water system or a natural water supply to a test chamber;

b) delivering a light emitting bioreagent sample from a bioreagent fermenter to said test chamber;

c) by at least one light detector detecting light emitted from said delivered bioreagent sample before it has been exposed to said water sample to provide a baseline light emission value for said bioreagent sample;

d) by at least one other light detector, detecting light emitted from said delivered bioreagent sample after it has been exposed to said water sample;

e) determining, where there has been a change in light emission as a result of contact of said delivered bioreagent sample with said water sample, that contaminants exist in said water sample; and f) removing said water sample and said bioreagent sample from said test chamber by a waste line in order to repeat the above process.

27. A continuous water monitoring system for detecting contaminants in a water supply comprising:

a) a feed line for delivering a sample of water from a water system or a natural water supply to a test chamber;

b) a test chamber;

c) a water sample conditioning means for altering the ionic strength of said sample of water before it is delivered to said test chamber;

d) a bioreagent fermenter in fluid communication with said test chamber for delivering a light emitting bioreagent, *Vibrio fischeri*, grown in said fermenter to said test chamber;

e) a light detection means for measuring light emitted from said bioreagent, comprising:

at least one light detector upstream of said test chamber;

at least one other light detector downstream of said bioreagent fermenter and said test chamber; and optionally at least one third light detector connected through a fluid communication means downstream of said second light detector: and f) a waste line for removing said sample and said bioreagent from said test chamber;

wherein a change in the light emitting properties of the bioreagent sample indicates that the water sample is contaminated.

\* \* \* \* \*